(12) United States Patent
Hong

(10) Patent No.: US 11,040,155 B2
(45) Date of Patent: Jun. 22, 2021

(54) INTEGRATED MONITORING AND MANAGEMENT SYSTEM FOR ENDOSCOPIC SURGERY

(71) Applicant: AFSMEDICAL GmbH Medizinproduktehandel, Teesdorf (AT)

(72) Inventor: Du Pyo Hong, Gimpo-si (KR)

(73) Assignee: AFSMEDICAL GMBH MEDIZINPRODUKTEHANDEL, Teesdorf (AT)

( * ) Notice: Subject to any disclaimer, the term of this patent is extended or adjusted under 35 U.S.C. 154(b) by 294 days.

(21) Appl. No.: 16/380,258

(22) Filed: Apr. 10, 2019

(65) Prior Publication Data
US 2019/0336709 A1    Nov. 7, 2019

(30) Foreign Application Priority Data

May 4, 2018 (KR) .......................... 10-2018-0051567

(51) Int. Cl.
| | |
|---|---|
| *A61B 1/32* | (2006.01) |
| *A61M 13/00* | (2006.01) |
| *A61B 90/90* | (2016.01) |
| *G16H 20/40* | (2018.01) |
| *G16H 40/63* | (2018.01) |
| *A61B 1/04* | (2006.01) |
| *A61B 1/313* | (2006.01) |

(Continued)

(52) U.S. Cl.
CPC ............. *A61M 13/003* (2013.01); *A61B 1/04* (2013.01); *A61B 1/3132* (2013.01); *A61B 5/01* (2013.01); *A61B 5/036* (2013.01); *A61B 17/0218* (2013.01); *A61B 17/0487* (2013.01); *A61B 17/3423* (2013.01); *A61B 90/90* (2016.02); *A61F 2/0063* (2013.01); *A61F 13/36* (2013.01); *G16H 20/40* (2018.01); *G16H 40/63* (2018.01); *A61B 2562/029* (2013.01); *A61M 2205/3306* (2013.01); *A61M 2205/3344* (2013.01); *A61M 2205/3368* (2013.01)

(58) Field of Classification Search
CPC combination set(s) only.
See application file for complete search history.

(56) References Cited

U.S. PATENT DOCUMENTS

2010/0081875 A1* 4/2010 Fowler ............... A61B 1/00188
600/114

FOREIGN PATENT DOCUMENTS

| JP | 2015150154 | 8/2015 |
|---|---|---|
| JP | 5975504 | 4/2017 |

(Continued)

*Primary Examiner* — Sameh R Boles
(74) *Attorney, Agent, or Firm* — Cantor Colburn LLP

(57) ABSTRACT

Provided is an integrated monitoring and management system for endoscopic surgery, in which the system simultaneously monitors and manages the surgical environment such as pressure, temperature, humidity, smoke, and the like inside the human body, and the type and access of surgical instruments used for surgery throughout the surgical procedure at the time of endoscopic surgery, such that an optimal surgical environment is maintained according to a monitoring result, and when an accident occurrence factor is monitored during the surgical procedure, it is possible to prevent an accident from occurring by informing of the accident occurrence factor, and it is possible to quantify a safe and successful surgical procedure by analyzing accumulated big data.

3 Claims, 2 Drawing Sheets

(51) Int. Cl.
  *A61B 5/01*   (2006.01)
  *A61B 5/03*   (2006.01)
  *A61B 17/02*  (2006.01)
  *A61B 17/04*  (2006.01)
  *A61B 17/34*  (2006.01)
  *A61F 2/00*   (2006.01)
  *A61F 13/36*  (2006.01)

(56) References Cited

FOREIGN PATENT DOCUMENTS

| | | |
|---|---|---|
| JP | 2018061858 | 4/2018 |
| KR | 101815689 | 1/2008 |
| KR | 101525126 | 6/2015 |
| KR | 20180023525 | 3/2018 |

* cited by examiner

INTEGRATED MONITORING AND MANAGEMENT SYSTEM FOR ENDOSCOPIC SURGERY

BACKGROUND OF THE INVENTION

Field of the Invention

The present invention relates to an integrated monitoring and management system for endoscopic surgery, in which the system simultaneously monitors and manages the surgical environment such as pressure, temperature, humidity, smoke, and the like inside the human body, and the type and access of surgical instruments used for surgery throughout the surgical procedure at the time of endoscopic surgery, such that an optimal surgical environment is maintained according to a monitoring result, and when an accident occurrence factor is monitored during the surgical procedure, it is possible to prevent an accident from occurring by informing of the accident occurrence factor, and it is possible to quantify a safe and successful surgical procedure by analyzing accumulated big data.

Description of the Related Art

In general, when performing endoscopic surgery, a hole is punctured in a human body instead of cutting a patient's body, and a retractor is inserted into the punctured hole to expand a diameter of the hole, so that surgical instruments (endoscopes, scissors, forceps, cameras, etc.) can be inserted through the retractor.

Although minimizing surgical scars, endoscopic surgery has many limitations because surgical procedure can be performed only through the retractor that expands the hole in the human body.

Thus, a surgeon or assistant (usually a nurse) who assists the surgeon must check and monitor the surgical environment and various surgical instruments used in the surgery, and take appropriate care and action accordingly.

For example, by checking a pressure of gas of the human body to secure a surgical space in the human body, when the pressure is lowered (that is, when the surgical space of the human body becomes narrower), the gas is injected into the human body to increase the pressure (that is, to widen the surgical space of the human body), and when smoke is generated in the surgical space of the human body and covers the field of vision, the smoke gas in the human body is discharged to the outside and fresh gas is injected into the human body simultaneously, so as to remove the smoke. Further, the types and quantity of surgical instruments inserted into the human body for surgery are checked and the types and quantity of the surgical instruments removed from the human body are checked, such that an accident that the surgical instruments are left in the human body after suture is prevented.

Monitoring of the surgical environment, and the subsequent management and action are currently performed by the surgeon and his or her assistant, and therefore high concentration and attention are required to prevent medical accidents.

Further, in the case of surgical operation, the data on the success of the operation according to the surgical environment, the condition of the patient, the surgical procedure, etc., the progress of the patient, and the like is poor. This is because it is difficult to dataficate detailed various surgical procedures and approaches by collecting data on the surgical procedures and approach and analyzing the collected data as the detailed surgical procedures and approach, such as surgical instruments used, use duration, and timing of use, are all different depending on the surgeon although surgical surgery roughly has the same surgical procedures and approach depending on the type of surgery.

Even when surgical surgery of the same type is performed in similar procedures and methods, the success rate is different depending on the doctor and the recovery period is different even in patients with similar conditions.

Thus, it may be of great help in surgical surgery to establish data quantifying the detailed surgical procedures and surgical procedures that can increase the success rate according to the surgical environment and the patient's condition, but this data has not yet been established.

For reference, there have been disclosed various types of retractor for endoscopic surgery, such as "Wound retractor for endoscopic surgery" of Korean Patent Application Publication No. 10-2018-0023525, "Trocar assembly" of Korean Patent No. 10-1525126, "Single port for endoscopic surgery" of Korean Patent No. 10-1815689, and the like.

In the prior art, there has not been provided the function to integrally monitor the surgical environment such as pressure, temperature, humidity, smoke inside the human body, and the types of surgical instruments used for surgery, the timing and frequency of use thereof, and whether the instruments are removed from the human body throughout the surgical procedure from the beginning to the end of endoscopic surgery, and manage and take measures accordingly.

The foregoing is intended merely to aid in the understanding of the background of the present invention, and is not intended to mean that the present invention falls within the purview of the related art that is already known to those skilled in the art.

SUMMARY OF THE INVENTION

Accordingly, the present invention has been made keeping in mind the above problems occurring in the related art, and an object of the present invention is to provide an integrated monitoring and management system for endoscopic surgery, in which the system integrally monitors and manages the surgical environment and the types of surgical instruments throughout the surgical procedure of the endoscopic surgery, such that an optimal surgical environment is maintained, the occurrence of medical accidents are prevented, the burden on the surgeon and assistant is reduced, and it is possible to help surgical surgery by analyzing the accumulated big data and detecting the successful surgical method.

In order to achieve the above objects, according to some aspect of the present invention, there is provided an integrated monitoring and management system for endoscopic surgery, the system including: a retractor including a penetrating member penetrating through a human body, and a guide member provided at an upper portion of the penetrating member to guide a surgical instrument to be inserted into the human body through the penetrating member; a sensor group provided at a lower portion of the penetrating member to sense surgical environment information inside the human body; an access monitoring unit including a readable member attached to the surgical instrument, and a reader provided in the guide member to monitor insertion and withdrawn of the surgical instrument by reading the readable member; and a controller configured to collect and analyze the surgical environment information, and insertion and withdrawn information of the surgical instrument from the sensor group and the reader, and inform of the information, wherein the sensor group includes a camera for taking an image of the inside of the human body, and a pressure sensor for sensing a pressure inside the human body, the system further comprises a supply and exhaust unit for supplying gas to the human body or discharging gas from the human body, and the controller analyzes the image taken by the camera and a pressure value sensed by the pressure sensor to control operation of the supply and exhaust unit, so as to keep the pressure of the human body constant and ensure a field of view of the camera.

The surgical instrument, to which the readable member is attached, may include gauze, a suture clip, and a mesh, and the controller may count the number of the surgical instruments inserted into the human body.

According to the integrated monitoring and management system for endoscopic surgery of the present invention is advantageous in that since the surgical environment information on images, temperature, humidity, pressure, etc. inside the human body, and the type, access of surgical instruments used for surgery and timing of use are integrally monitored and managed through the sensor group, an optimal surgical environment is maintained to facilitate safe surgery, and it is possible to prevent a medical accident from occurring by informing of a risk factor, and since the types and quantity of surgical instruments inserted into and removed from the human body, frequency of use, and use duration are monitored, it is possible to prevent a medical accident in which the suture is performed while leaving a surgical instrument.

The integrated monitoring and management system for endoscopic surgery of the present invention is further advantageous in that since big data is accumulated for a large number of patients by integrally monitoring and managing the surgical environment and surgical instruments, and the surgical environment and the specific surgical procedures and approaches that are favorable for the patient's recovery and the success rate according to the patient's characteristics are quantified by analyzing the big data, it is of great help in surgical surgery, and very useful invention for industrial development.

BRIEF DESCRIPTION OF THE DRAWINGS

The above and other objects, features, and other advantages of the present invention will be more clearly understood from the following detailed description when taken in conjunction with the accompanying drawings, in which.

DETAILED DESCRIPTION OF THE INVENTION

Figure 1:
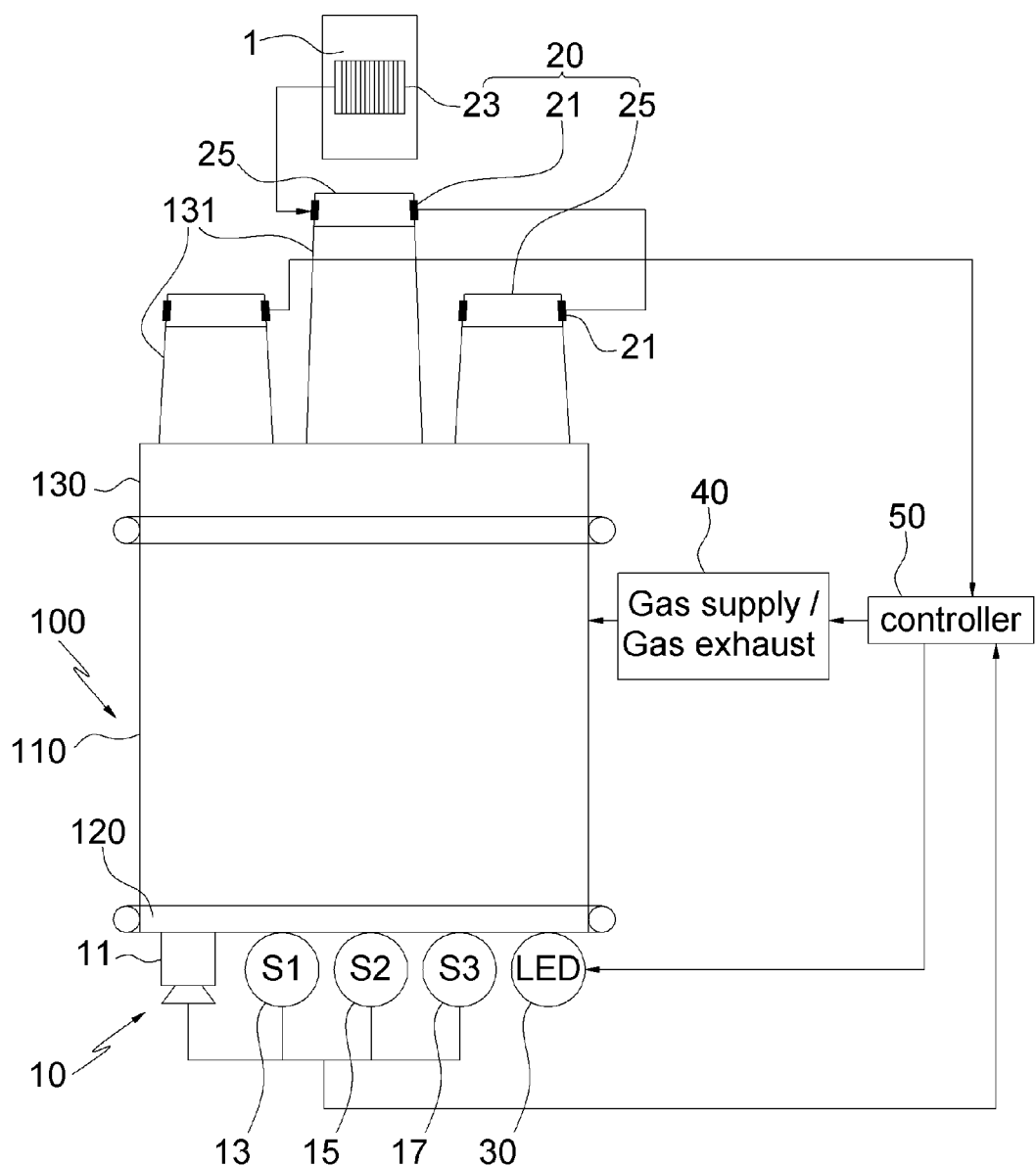
FIG. 1 is a schematic diagram showing an integrated monitoring and management system for endoscopic surgery according to the present invention.

Hereinbelow, reference will be made in detail to an integrated monitoring and management system for endoscopic surgery according to the present invention, with reference to the accompanying drawings.

Before describing the integrated monitoring and management system for endoscopic surgery of the present invention in more detail, the present invention will be described in detail based on aspects (or embodiments). The present invention may, however, be embodied in many different forms and should not be construed as being limited to only the embodiments set forth herein, but should be construed as covering modifications, equivalents or alternatives falling within ideas and technical scopes of the present invention.

In the figures, like reference numerals, particularly, tens and units, or reference numerals having like tens, units and letters refer to like elements having like functions throughout, and unless the context clearly indicates otherwise, elements referred to by reference numerals of the drawings should be understood based on this standard.

Also, for convenience of understanding the elements, in the figures, sizes or thicknesses may be exaggerated to be large (or thick), may be expressed to be small (or thin), or may be simplified for clarity of illustration, but due to this, the protective scope of the present invention should not be interpreted narrowly.

The terminology used herein is for the purpose of describing particular aspects (or embodiments) only and is not intended to be limiting of the present invention. As used herein, the singular forms are intended to include the plural forms as well, unless the context clearly indicates otherwise.

It will be further understood that the terms "comprises", "comprising", "includes", and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms including technical and scientific terms used herein have the same meaning as commonly understood by one of ordinary skill in the art to which the present invention belongs. It will be further understood that terms used herein should be interpreted as having a meaning that is consistent with their meaning in the context of this specification and the relevant art and will not be interpreted in an idealized or overly formal sense unless expressly so defined herein.

As shown in the drawings, an integrated monitoring and management system for endoscopic surgery according to the present invention includes a retractor 100, a sensor group 10, an access monitoring unit 20, a supply and exhaust unit 40, a lighting unit 30, and a controller 50.

The retractor 100 is inserted into a hole punctured in a human body of a patient to expand the diameter of the hole and maintain the expanded state, such that surgical instruments are inserted into the human body through the hole (more specifically, the inside of the retractor 100 expanding the hole) and are removed from the human body.

There are various types of retractors 100 such as trocar, retractor, and cannula.

The retractor 100 includes a penetrating member 110, an anti-separation member 120, and a guide member 130.

The penetrating member 110 penetrates through a hole punctured in a patient's body for endoscopic surgery, and expands the diameter of the hole to form a passage that allows a surgical instrument 1 to be inserted into the human body through the hole (specifically, through the inside of the penetrating member 110 penetrating through the hole).

The penetrating member 110 is usually made of hard material in the case of a trocar, and is usually made of a soft material in the case of a retractor.

In the drawings, it is shown that the penetrating member 110 is made of a soft material such as silicone and has a cylindrical structure.

The anti-separation member 120 is provided at a lower portion of the penetrating member 110 and is inserted into the patient's body through the punctured hole in the human body.

The anti-separation member 120 has a diameter of about 5 mm to 10 mm and is formed in an annular ring shape so as to be caught on an inner wall of the human body to ensure the retractor 100 is not easily detached from the human body when impact is applied to the retractor 100 in unintended situations.

The guide member 130 is provided at an upper portion of the penetrating member 110 to guide the surgical instrument 1 to be inserted into the human body through the penetrating member 110.

The guide member 130 is provided with a port 131 for tightly covering the outer surface of the surgical instrument 1 to prevent leakage of gas.

A cap 25 is coupled to an upper portion of the port 131, and the cap 25 is provided with a reader 21 for reading a readable member 23 attached to the surgical instrument 1 passing the port.

Referring to the drawing, the upper portion of the penetrating member 110 is provided with an outer ring 111 that is caught outside the periphery of the hole of the human body, and the outer ring 111 is provided at the upper portion thereof with a coupler 115 to which the guide member 130 is detachably coupled.

The sensor group 10 is provided in the anti-separation member 120 of the retractor 100 to sense the surgical environment information inside the human body and transmit the information to the controller 50.

The sensor group 10 includes a camera 11 for taking images of the inside of the human body, a pressure sensor 13 for sensing the pressure inside the human body, a temperature sensor 15 for sensing the temperature, and a humidity sensor 17 for sensing the humidity.

The camera 11 takes images of the inside of the human body to monitor whether there is smoke in the surgical space, whether there is a bleeding site, or whether there is a coagulation of blood or body fluids.

The pressure sensor 13 senses the pressure inside the human body and transmits it to the controller 50 such that the pressure of the human body remains constant. In other words, the pressure sensor ensures that the surgical space created by the gas supplied to the human body remains constant without being reduced or excessively inflated.

The temperature sensor 15 and the humidity sensor 17 sense the temperature and humidity inside the human body, respectively, and transmit them to the controller 50 so that the condition of the patient under operation can be checked.

The access monitoring unit 20 monitors the insertion of the surgical instrument 1 into the human body through the retractor 100 and separation thereof, and the type of the surgical instrument 1 inserted into and removed from the human body, and transmits the monitored information to the controller 50. The controller 50 then analyzes what kind of surgical instrument 1 was used, when surgical instrument 1 was inserted and removed, how long it stayed in the human body, the number of times each surgical instrument 1 was used, and whether there is a surgical instrument 1 that was not removed from the human body.

The access monitoring unit 20 is constituted by the readable member 23 attached to the surgical instrument 1, and the reader 21 provided in the guide member 130 of the retractor 100 to read the readable member 23 attached to the surgical instrument 1 passing through the retractor 100.

The readable member 23 may be a bar code, a QR code, a magnetic sheet, or an IC chip. The readable member 23 contains information about a type of the surgical instrument 1, and a unique serial number.

The reader 21 is mounted within the cap 25 that is coupled to the upper portion of the port 131 of the guide member 130 through which the surgical instrument 1 passes, extracts the information on the type and the serial number of the surgical instrument 1 by reading the readable member 23 such as a bar code or a magnetic sheet attached to the passing surgical instrument 1, and transmits the extracted information to the controller 50.

In surgery, a medical accident in which the suture is performed while leaving a surgical instrument 1, such as scissors, forceps, gauze, and clips, in the human body is very fatal. Further, the input quantity of meshes that prevent long-term adhesions or prevent hernias should be checked. Thus, it is important to accurately monitor and check the access of the surgical instrument 1 to the human body without error.

The supply and exhaust unit 40 supplies gas to the human body or discharges gas in the human body to the outside.

The supply and exhaust unit 40 includes: a tube for providing a passage through which gas is supplied and discharged; a filter connected to the tube to filter and remove foreign matter of the gas supplied to the human body; and a supply and exhaust pump (not shown) connected to the tube and configured to provide power to supply or discharge the gas.

The lighting unit 30 is provided in the anti-separation member 120 to illuminate the inside of the human body. As a lighting unit, it may be desirable to use a chip LED that is small, high in illumination, and capable of adjusting the illuminance.

The controller 50 collects and analyzes the surgical environment information acquired and transmitted by the sensor group 10 and the insertion and withdrawn information of the surgical instrument 1 monitored and transmitted by the access monitoring unit 20, and provides the various collected and analyzed surgical information to a surgeon and an assistant, and when the analysis finds that there is a risk factor, a warning is given through alarm sound or a flashing lamp, and when the analysis finds that an action is required to create an optimal surgical environment, the action is automatically taken.

For an example, the controller 50 displays an image taken by the camera 11 of the sensor group 10 in real time on a monitor, and displays a pressure value sensed by the pressure sensor 13 and a temperature value sensed by the temperature sensor 15 on the monitor.

For another example, when it is sensed that the surgical instrument 1 used to suture the hole of the human body is inserted, but it is analyzed that the surgical instrument 1 or gauze not related to the suture is left in the human body, a warning is given to a surgeon and the like through alarm sound or a flashing lamp.

For a further example, when the pressure sensed by the pressure sensor 13 falls below a reference value, the supply and exhaust unit 40 is driven to supply gas to the human body to increase the pressure; when smoke is detected from the camera 11 image, the supply and exhaust unit 40 is driven to discharge and remove the smoke gas from the human body while injecting external fresh gas into the human body; and when the illumination recognized by the camera 11 image is low, the illumination of the lighting is increased.

Figure 2:
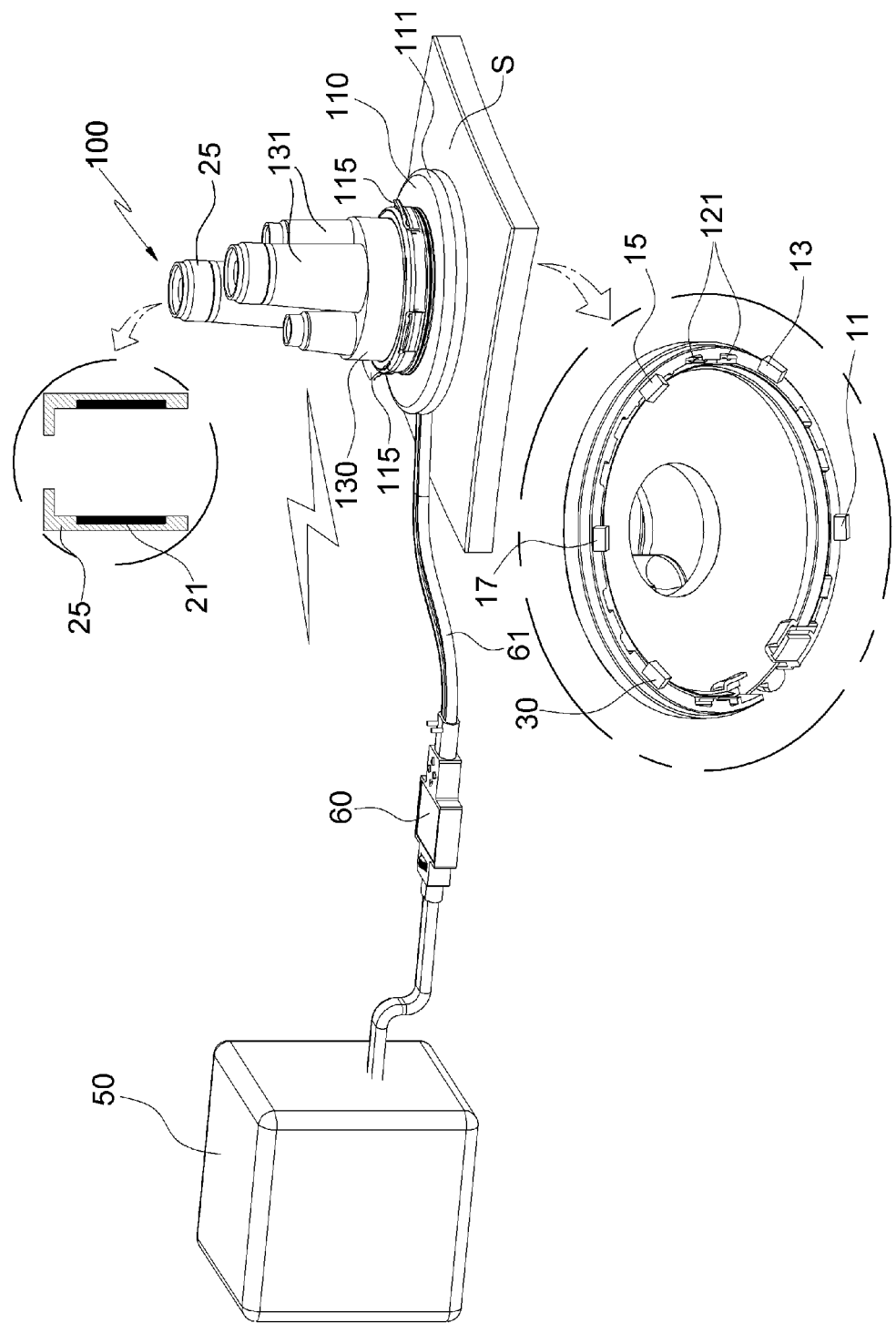
FIG. 2 is a perspective view showing an example of a retractor according to the present invention.

FIG. 2 shows an example in which the retractor 100 according to the present invention is coupled to a human body S.

The outer ring 111 of the penetrating member 110 of the retractor 100 is connected with a cable 61 that is electrically connected to the sensor group 10 (11, 13, 15, and 17) and the lighting unit 30 provided in the anti-separation member 120 to supply power and transmit the sensed information to the controller 50.

The cable 61 is provided with a remote controller 60 that allows the controller 50 to be operated remotely. The remote controller 60 communicates with the controller 50 by being wired or wirelessly connected thereto. In the drawing, the wired connection is shown. When connected wirelessly, the remote controller will be provided with a battery that supplies power to the sensor group 10 and the lighting unit, and a communication module that wirelessly communicates with the controller.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An integrated monitoring and management system for endoscopic surgery, the system comprising:
    a retractor including a penetrating member penetrating through a human body, and a guide member provided at an upper portion of the penetrating member to guide a surgical instrument to be inserted into the human body through the penetrating member;
    a sensor group provided at a lower portion of the penetrating member to sense surgical environment information inside the human body;
    an access monitoring unit including a readable member attached to the surgical instrument, and a reader provided in the guide member to monitor insertion and withdrawn of the surgical instrument by reading the readable member; and
    a controller configured to collect and analyze the surgical environment information, and insertion and withdrawn information of the surgical instrument from the sensor group and the reader, and inform of the information,
    wherein the sensor group includes a camera for taking an image of the inside of the human body, and a pressure sensor for sensing a pressure inside the human body,
    the system further comprises a supply and exhaust unit for supplying gas to the human body or discharging gas from the human body, and
    the controller analyzes the image taken by the camera and a pressure value sensed by the pressure sensor to control operation of the supply and exhaust unit, so as to keep the pressure of the human body constant and ensure a field of view of the camera.

2. The system of claim 1, wherein the sensor group further includes a temperature sensor and a humidity sensor for sensing temperature and humidity inside the human body, respectively.

3. The system of claim 1, wherein the surgical instrument, to which the readable member is attached, includes gauze, a suture clip, and a mesh, and
    the controller counts a number of the surgical instruments inserted into the human body.

\* \* \* \* \*